(12) United States Patent
Yotoriyama et al.

(10) Patent No.: US 9,523,091 B2
(45) Date of Patent: Dec. 20, 2016

(54) NUCLEIC-ACID EXTRACTION METHOD AND NUCLEIC-ACID EXTRACTION CARTRIDGE

(75) Inventors: Tasuku Yotoriyama, Tokyo (JP); Tomohiko Nakamura, Tokyo (JP); Naohisa Sakamoto, Tokyo (JP); Kazumine Ito, Tokyo (JP); Tomoteru Abe, Tokyo (JP); Michihiro Ohnishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 620 days.

(21) Appl. No.: 13/533,348

(22) Filed: Jun. 26, 2012

(65) Prior Publication Data

US 2013/0020201 A1    Jan. 24, 2013

(30) Foreign Application Priority Data

Jul. 20, 2011   (JP) ................................. 2011-158991

(51) Int. Cl.
*C07H 21/00* (2006.01)
*B01D 59/42* (2006.01)
*C12N 15/10* (2006.01)

(52) U.S. Cl.
CPC ......... *C12N 15/1006* (2013.01); *C12N 15/101* (2013.01)

(58) Field of Classification Search
CPC .......................... C12N 15/1006; C12N 15/101
USPC ........................ 536/25.4; 204/450, 554, 565
See application file for complete search history.

(56) References Cited

U.S. PATENT DOCUMENTS

| 2004/0126783 A1* | 7/2004 | Bortolin et al. ................ 435/6 |
| 2006/0186055 A1* | 8/2006 | Kusumoto et al. .......... 210/695 |
| 2008/0121591 A1* | 5/2008 | Knight et al. ................ 210/748 |

FOREIGN PATENT DOCUMENTS

| JP | 07-051065 | 2/1995 |
| JP | 09-019292 | 1/1997 |
| JP | 2003-128691 | 5/2003 |
| JP | 2005-080555 | 3/2005 |

OTHER PUBLICATIONS

Simpson, Jr., L Steven, et al. "On-line Sample Preconcentration in Capillary Electrophoresis Fundamentals and Applications" Journal of Chromatography A, vol. 1184, (2008), pp. 504-541.
T. Stroink, et al., "On-line sample preconcentration in capillary electrophoresis, focused on the determination of proteins and peptides: a review," Journal of Chromatography A., Chapter 2, Jul. 20, 2011, pp. 51-70.

* cited by examiner

*Primary Examiner* — Jezia Riley
(74) *Attorney, Agent, or Firm* — Michael Best & Friedrich LLP

(57) ABSTRACT

The present disclosure provides a nucleic-acid extraction method for carrying out the following procedures in the same cell, the procedures including: performing an ultrasonic process on a sample containing a nucleic acid; adsorbing substances contained in the sample by making use of an adsorption carrier; and condensing the nucleic acid by damming the nucleic acid moving in an electrophoresis phenomenon. In accordance with the nucleic-acid extraction method, it is possible to carry out an ultrasonic process, an adsorption process and an electrophoresis process in the same cell. Thus, it is possible to eliminate an operation to transfer the sample from one cell to another one for each of the processes.

8 Claims, 4 Drawing Sheets

NUCLEIC-ACID EXTRACTION METHOD AND NUCLEIC-ACID EXTRACTION CARTRIDGE

BACKGROUND

In general, the present disclosure relates to a nucleic-acid extraction method and a nucleic-acid extraction cartridge. More particularly, the present disclosure relates to a method for extracting a nucleic acid from a sample by carrying out an ultrasonic process on the sample, a process of adsorbing foreign substances and the like from the sample and an electrophoresis process on the nucleic acid in the same channel and relates to a nucleic-acid extraction cartridge adopting the method.

Nucleic-acid amplification reaction methods such as a PCR (Polymerase Chain Reaction) method and a LAMP (Loop-Mediated Isothermal Amplification) method are applied to a variety of fields in the biotechnology. For example, diagnoses based on DNA and/or RNA base sequences are carried out in the medical field whereas DNA appraisements such identifications of genetically-engineered plants are put to practical use in the agricultural field.

In a nucleic-acid amplification reaction, a nucleic acid in a sample having a very small quantity is amplified with a high degree of efficiency in order to allow the acid to be detected. If the quantity of the nucleic acid contained in the sample is extremely small, however, the quantity may be smaller than a detection lower limit in some cases. In addition, if the concentration of the nucleic acid contained in the sample is very low, the acid may not be detected in some cases because the sample having a volume introducible into a reaction field does not contain an enough nucleic acid to be amplified. Problems raised in such cases can be solved by adoption of an effective method described as follows. The nucleic acid is refined, condensed and extracted in advance before being introduced into a reaction field.

As is generally known, methods in the past for extracting a nucleic acid include a method making use of phenol, chloroform or ethanol, a method making use of a column or a filter and a method making use of magnetic silica beads. The column and the filter are used for adsorbing the nucleic acid.

For example, Japanese Patent Laid-open No. 2005-080555 discloses a method for condensing a nucleic acid by making use of a porous carrier capable of adsorbing the nucleic acid. In addition, a method for condensing a nucleic acid in a capillary electrophoresis phenomenon is disclosed in "On-line sample preconcentration in capillary electrophoresis: Fundamentals and applications." Journal of Chromatography A., Vol. 1184 (2008) pp. 504-541.

SUMMARY

In the case of the method in the past making use of phenol, chloroform or ethanol, however, it is necessary to utilize a harmful organic solvent and it takes a lot of trouble to carry out a centrifugal separation process and the like. In addition, in the case of the method making use of either of a column and a filter which are each utilized for adsorbing the nucleic acid, the column and the filter are prone to a clogged state, causing operation inconvenience which raises a problem.

It is desirable to provide a nucleic-acid extraction method which allows operations to be carried out with ease and is capable of extracting a nucleic acid from a sample in a short period of time with a high degree of efficiency.

In order to solve the problems described above, the present disclosure provides a nucleic-acid extraction method for carrying out the following procedures in the same cell, the procedures including:

performing an ultrasonic process on a sample containing a nucleic acid;

adsorbing substances contained in the sample by making use of an adsorption carrier; and condensing the nucleic acid by damming the nucleic acid moving in an electrophoresis phenomenon.

As described above, the nucleic-acid extraction method is capable of carrying out the ultrasonic process, the adsorption process and the electrophoresis process in the same cell. The ultrasonic nucleic-acid extraction method allows the work to translocate the sample from the inside of the cell to another cell for each of the processes to be eliminated.

In addition, it is desirable to make use of a cation exchange resin or a zeolite as the adsorption carrier. In addition, it is desirable to make use of a strongly acidic cation exchange resin as the cation exchange resin.

In addition, it is desirable to carry out the ultrasonic process after blending bead particles in the sample. In addition, it is desirable that the substances are each a foreign substance other than the nucleic acid.

In addition, it is desirable that the procedure of performing the ultrasonic process on the sample is a procedure of performing the ultrasonic process on the sample by diluting the sample by making use of a buffer solution, and that the pH of the buffer solution has a value in a range of 4.0 to 8.0. In addition, it is desirable that the buffer solution contains a thickening agent. In addition, it is desirable that the thickening agent contains polyethylene glycol and/or hydroxy ethyl cellulose. It is to be noted that the cell cited above mainly implies a cartridge for extracting a nucleic acid as will be described later. In addition, the foreign substance mentioned before mainly implies specific substances detected in analyses of the nucleic acid contained in the sample. The specific substances include various kinds of unnecessary protein, peptide, sugar, salt and metal ions, to mention a few.

In addition, in order to solve the problems described above, the present disclosure also provides a nucleic-acid extraction cartridge including:

a channel allowing a sample containing a nucleic acid to be introduced into the channel;

electrodes each provided on one of the ends of the channel;

a damming section configured to divide the channel into a negative-electrode side area and a positive-electrode side area and dam the nucleic acid;

an adsorption carrier provided in the negative-electrode side area to adsorb substances contained in the sample; and an ultrasonic-wave generation section configured to carry out an ultrasonic process on the sample.

In addition, the ultrasonic-wave generation section can be implemented as the same member as one of the electrodes. In addition, it is desirable that the damming section is a dialysis membrane or a polymer gel. In addition, it is desirable that the ultrasonic-wave generation section is an ultrasonic probe or an ultrasonic horn.

As described above, the present disclosure provides a nucleic-acid extraction method which allows operations to be carried out with ease and is capable of extracting a nucleic acid from a sample in a short period of time with a high degree of efficiency.

DETAILED DESCRIPTION OF THE PREFERRED EMBODIMENTS

Preferred embodiments of the present disclosure are explained as follows. It is to be noted that embodiments to be described below as the embodiments of the present disclosure are merely typical implementations of the present disclosure and not to be interpreted as limitations narrowing the scope of the disclosure. The embodiments are described in the following order.
1. A nucleic-acid extraction cartridge according to a first embodiment of the present disclosure, a nucleic-acid extraction method for the cartridge and a method for manufacturing the nucleic-acid extraction cartridge
 (1) Nucleic-acid extraction cartridge
 (2) Nucleic-acid extraction method
 (3) Method for manufacturing the nucleic-acid extraction cartridge
2. A nucleic-acid extraction cartridge according to a modified version of the first embodiment of the present disclosure, a nucleic-acid extraction method for the cartridge and a method for manufacturing the nucleic-acid extraction cartridge 1. A Nucleic-Acid Extraction Cartridge According to a First Embodiment of the Present Disclosure, a Nucleic-Acid Extraction Method for the Cartridge and a Method for Manufacturing the Nucleic-Acid Extraction Cartridge
(1) Nucleic-Acid Extraction Cartridge FIG. 1 is an explanatory model diagram showing the configuration of a nucleic-acid extraction cartridge 1 according to a first embodiment of the present disclosure.

Figure 1:
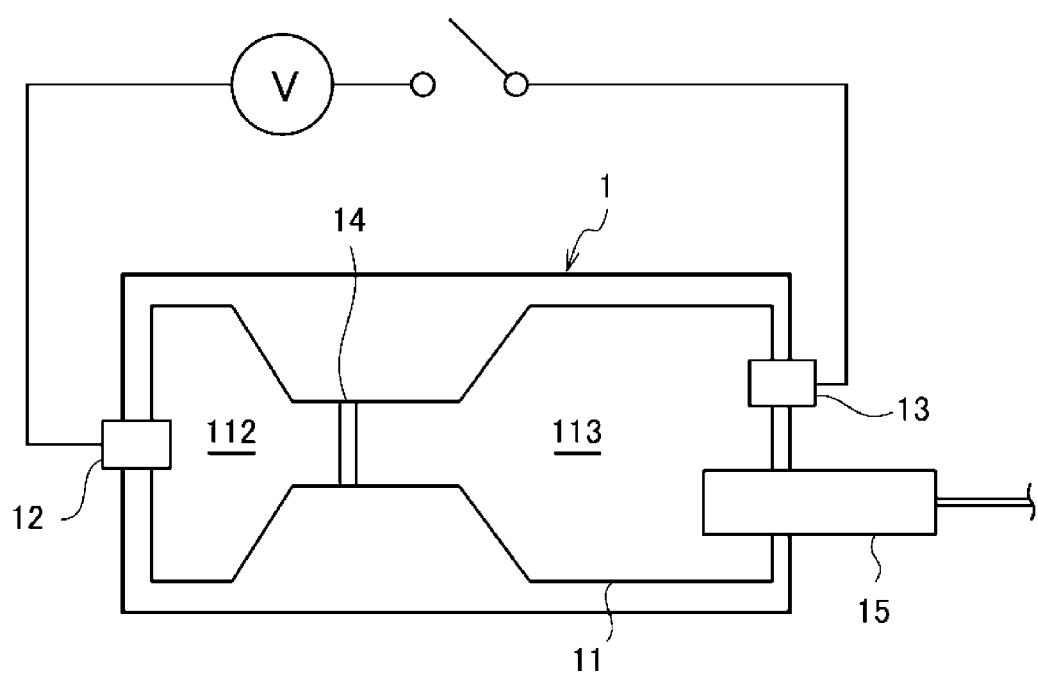
FIG. 1 is an explanatory model diagram showing the configuration of a nucleic-acid extraction cartridge according to a first embodiment of the present disclosure.

A nucleic-acid extraction cartridge denoted by reference numeral 1 in FIG. 1 has a channel 11 formed in a base material, a positive electrode 12 and a negative electrode 13. The positive electrode 12 and the negative electrode 13 are each provided on one of the two ends of the channel 11. A sample can be introduced into the inside of the channel 11. A dialysis membrane 14 is provided between the positive electrode 12 of the channel 11 and the negative electrode 13 of the channel 11. The dialysis membrane 14 is provided between the positive electrode 12 and the negative electrode 13, dividing the inside of the channel 11 into a positive-electrode side area 112 and a negative-electrode side area 113. In addition, the positive electrode 12 and the negative electrode 13 are connected to a power supply V in a configuration allowing a voltage to be applied to or removed from the sample introduced into the inside of the channel 11.

On top of that, an adsorption carrier is accommodated in the negative-electrode side area 113 of the channel 11. In addition, an ultrasonic horn 15 is provided in the negative-electrode side area 113.

The characteristics of the base material can be the same as those of glass or various kinds of plastic such as polypropylene, polycarbonate, cycloolefin polymer and polydimethylsiloxane.

As described above, the dialysis membrane 14 divides the inside of the channel 11 into the positive-electrode side area 112 and the negative-electrode side area 113. In accordance with a nucleic-acid extraction method provided by the present disclosure to serve as a method making use of the nucleic-acid extraction cartridge 1, a nucleic acid migrates from the negative electrode 13 to the positive electrode 12 in an electrophoresis movement and is dammed by the dialysis membrane 14. For this reason, the sample is introduced into the negative-electrode side area 113 of the channel 11.

The shape of the channel 11 is not prescribed in particular. However, the shape of the negative-electrode side area 113 can be typically like one shown in FIG. 1. As shown in the figure, the shape of the negative-electrode side area 113 is gradually depressed in the direction from the negative electrode 13 to the dialysis membrane 14.

An adsorption carrier is accommodated in the negative-electrode side area 113. The adsorption carrier is not prescribed in particular. That is to say, the adsorption carrier can be any carrier as long as the carrier is capable of adsorbing substances other than the nucleic acid in a sample. Typical proper examples of the adsorption carrier are a cation exchange resin or a zeolite. By accommodating such an adsorption carrier in the negative-electrode side area 113 as described above, in accordance with a nucleic-acid extraction method provided by the present disclosure, in an adsorption process, it is possible to eliminate predetermined substances contained in the sample in the negative-electrode side area 113 prior to an electrophoresis process of the sample. The predetermined substances are mainly substances other than the nucleic acid contained in the sample.

In addition, it is desirable that bead particles are accommodated in the negative-electrode side area 113. By accommodating bead particles in the negative-electrode side area 113, in accordance with the nucleic-acid extraction method provided by the present disclosure, the ultrasonic process of the sample can be carried out with a higher degree of precision as will be described later.

Each of the positive electrode 12 and the negative electrode 13 is made of a proper material containing gold (Au) added thereto in an electrical plating process, a sputtering process or an evaporation process or platinum. As an alternative, each of the positive electrode 12 and the negative electrode 13 is made of a corrosion-proof material such as graphite, titan or stainless steel.

The dialysis membrane 14 is a typical damming section according to the present disclosure. The damming section is not prescribed in particular. That is to say, the damming section can be any member as long as the member is capable of damming the nucleic acid contained in the sample during an electrophoresis process. In addition, the damming section does not have to be the dialysis membrane 14. Instead, the damming section can also be a porous membrane such as a reverse osmosis membrane, a semipermeable membrane, an ion exchange membrane or the like. As an alternative, the damming section can also be a porous membrane made of cellulose, poly acrylic nitrile, ceramic, zeolite, polysulfone, polyimide, palladium or the like. In addition, it is also possible to make use of a polymer gel in place of the dialysis membrane 14.

The polymer gel is properly made of poly acrylic amide. It is desirable that the polymer gel is made of poly acrylic amide containing an anionic functional group. It is even more desirable that the polymer gel is made of poly acrylic amide containing an anionic functional group having an acid dissociation constant (pKa) in a range of 1 to 5. It is to be noted that, in this embodiment, the poly acrylic amide implies acrylic amide or meta acrylic amide.

The anionic functional group is not prescribed in particular. Typical examples of the anionic functional group are a carbon acid such as an acetic acid, a propionic acid or a butyric acid, a polybasic acid such as an oxalic acid or a phthalic acid, a hydroxy acid such as a citric acid, a glycol acid or a lactic acid, an unsaturated polybasic acid or an unsaturated acid such as an acrylic acid or a methacrylic acid, an amino acid such as glycine, the partial ester of a phosphoric acid, the partial ester of a vitriolic acid, a phosphonate and a sulfonic acid.

To put it concretely, typical examples of the carbon acid are an aliphatic monocarboxylic acid, an aliphatic or aromatic dicarboxylic acid, an unsaturated carboxylic acid, a substituted benzoic acid group and a poly-carboxylic acid as well as its derivatives. Typical examples of the aliphatic monocarboxylic acid are a formic acid with a pKa of 3.55, an acetic acid with a pKa of 4.56, a propionic acid with a pKa of 4.67, a butane acid with a pKa of 4.63, a pentene acid with a pKa of 4.68, a hexane acid with a pKa of 4.63, a heptane acid with a pKa of 4.66, a palmitic acid with a pKa of 4.64 and a stearic acid with a pKa of 4.69. Typical examples of the aliphatic or aromatic dicarboxylic acid are a succinic acid with a $pKa_1$ of 4.00 and a $pKa_2$ of 5.24, a glutaric acid with a $pKa_1$ of 4.13 and a $pKa_2$ of 5.03, an adipic acid with a $pKa_1$ of 4.26 and a $pKa_2$ of 5.03, a pimelic acid with a $pKa_1$ of 4.31 and a $pKa_2$ of 5.08, a suberic acid with a $pKa_1$ of 4.35 and a $pKa_2$ of 5.10, an azelaic acid with a $pKa_1$ of 4.39 and a $pKa_2$ of 5.12, a malic acid with a $pKa_1$ of 3.24 and a $pKa_2$ of 4.71 and a terephthalic acid with a $pKa_1$ of 3.54 and a $pKa_2$ of 4.46. Typical examples of the unsaturated carboxylic acid are a crotonic acid with a pKa of 4.69, an acrylic acid with a pKa of 4.26 and a methacrylic acid with a pKa of 4.66. Acids included in the substituted benzoic acid group are an anisic acid with a pKa of 4.09, an m-amino benzoic acid with a $pKa_1$ of 3.12 and a $pKa_2$ of 4.74, an m- and p-chloro benzoic acid with a $pKa_1$ of 3.82 and a $pKa_2$ of 3.99, a hydroxy benzoic acid with a $pKa_1$ of 4.08 and a $pKa_2$ of 9.96. A typical example of the poly-carboxylic acid is a citric acid with a $pKa_1$ of 2.87, a $pKa_2$ of 4.35 and a $pKa_3$ of 5.69.

As the acrylic amide monomer containing the anionic functional group, the acrylic amide alkane sulfone acid is particularly desirable. The sulfone acid is a sulfone acid having a polymerizable unsaturated radical. Typical examples of the sulfone acid having a polymerizable unsaturated radical are a styrene sulfone acid with a pKa of −2.8, an m-aniline sulfone acid with a pKa of 3.74, a p-aniline sulfone acid with a pKa of 3.23 and a 2-(meta) acryl amide-2-alkyl propane sulfone acid with a carbon count of 1 to 4 or, to put it more concretely, a 2-acryl amide-2-methyl propane sulfone acid with a pKa of −1.7.

It is desirable that the concentration of the anionic functional group in the poly-acrylic amide gel has a value in a range of 0 to 30%. In this case, the concentration is defined as a relative mass expressed in terms of %.

The ultrasonic horn 15 is a typical example of the ultrasonic-wave generation section provided by the present disclosure to serve as a section for carrying out an ultrasonic process on a sample. The shape (and other attributes) of the ultrasonic horn 15 serving as the ultrasonic-wave generation section are not prescribed in particular. That is to say, the ultrasonic-wave generation section can have any attributes including the shape as long as the ultrasonic-wave generation section is capable of carrying out an ultrasonic process on a sample in accordance with the nucleic-acid extraction method provided by the present disclosure. For example, as the ultrasonic-wave generation section, it is also possible to make use of an ultrasonic probe or the like in place of the ultrasonic horn 15. In the case of the first embodiment of the present disclosure and a modified version of the first embodiment, in most descriptions given below, it is assumed that the ultrasonic horn 15 serves as the ultrasonic-wave generation section according to the present disclosure.

(2) Nucleic-Acid Extraction Method

Next, procedures of a nucleic-acid extraction method according to the present disclosure are explained by referring to FIGS. 2A to 2D as follows.

Prior to the explanation of the nucleic-acid extraction method according to the present disclosure, first of all, the following description explains a nucleic-acid extraction method based on a technology related to the technology provided by the present disclosure.

A typical example of the nucleic-acid extraction method based on a related technology is an AGPC (Acid guanidinium Thiocyanate-Phenol-Chloroform Extraction) method. In accordance with the AGPC method, first of all, a heating treatment is carried out on an alkalized sample obtained as a result of blending an alkalized agent. Then, a protein material is dissolved by making use of an enzyme such as a protease. Subsequently, the protein material, a sugar and a lipophilic substance are removed by adoption of a phenol-chloroform extraction method. In the safety and quickness fields, however, this method is desired to be improved. For example, the types of samples in use and the adequacy of processing for multi-analytes are desired to be made better.

In addition, there is also provided a method in accordance with which, on the particle surface of silica or the like, the nucleic acids of the DNA, the RNA and the like are physically or chemically joined together (or adsorbed to the surface) and the DNA, the RNA and the like are physically or chemically separated from the sample (refer to documents such as Japanese Patent Laid-open No. Hei 7-51065). In accordance with this method, however, if magnetic silica particles suspended in the solution are dispensed from the sample container to the micro tube, the dispensation is desired to be completed by the end of a period in which the particle liquid solution is agitated in order to disperse the particles. In addition, the concentration of the solution dispensed as described above hardly becomes uniform and the concentration of particles tends to vary in accordance with the dispensation timing. Thus, for quantitative analyses, this method is desired to be improved.

On top of that, as for the particles used for isolating the nucleic acid, there is also provided a method in accordance with which, the nucleic acid is retrieved by making use of a magnetic force. For example, there is also provided a method in accordance with which, magnetic silica particles for forming an object membrane made of polymerizable silane allowing a nucleic acid or the like to be covalently bonded are used on the surface of center-core infinitesimal particles made of a superparamagnetic iron oxide (refer to documents such as Japanese Patent Laid-open No. Hei 9-19292).

In addition, in the gene testing industry, there is also provided a nucleic-acid extraction method in accordance with which, silica is formed into the shape of a membrane filter and is incorporated in a spin column, and then a suction filtration process or a centrifugal filtration process is carried out. Furthermore, there is a method making use of a polymer porous membrane in place of the silica membrane filter (refer to documents such as Japanese Patent Laid-open No. 2003-128691). However, these methods require a number of processes, a lot of cleansing liquid and an apparatus such as a pump or a centrifuge. Thus, the size of the entire apparatus increases.

In order to solve the problems described above, the present disclosure provides a nucleic-acid extraction method to be described below in detail as a result of earnest efforts made by inventors of the present disclosure. The nucleic-acid extraction method allows operations to be carried out with ease and is capable of extracting a nucleic acid from a sample in a short period of time with a high degree of efficiency.

Figure 2A:
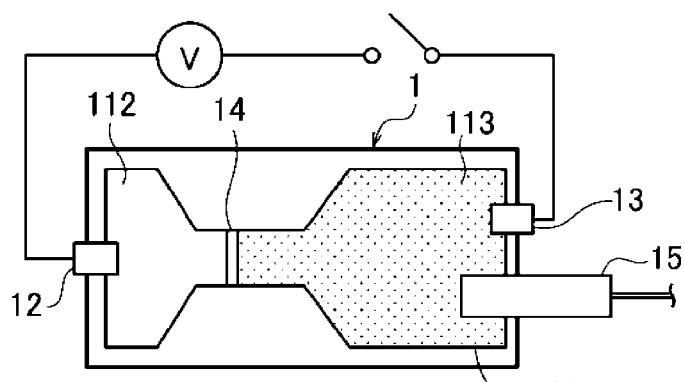
FIGS. 2A to 2D are explanatory model diagrams to be referred to in description of procedures of a nucleic-acid extraction method according to the first embodiment of the present disclosure.

In accordance with the nucleic-acid extraction method provided by the present disclosure, first of all, as shown in FIG. 2A, a sample containing a nucleic acid is introduced into the negative-electrode side area 113 between the dialysis membrane 14 and the negative electrode 13 which are employed in the channel 11. At that time, the channel 11 has been filled up with a buffer solution for diluting the sample to be subjected to an electrophoresis process. The sample introduced into the negative-electrode side area 113 is liquid made of a biological material. Typical examples of the liquid made of a biological material are swab, mouth swab, sputum, whole blood, blood serum, blood plasmas, peripheral blood monocytic cells, liquor cerebrospinalis, shits, urine, sweat, spermatic fluid, bacterial broth, cultivated cells and biopsy tissues. In addition, another typical example of the liquid made of a biological material is fluids such as liquid contained in food, water, earth medium, ocean water, lake water and river water. Thus, in some cases, the sample liquid also contains substances disturbing nucleic-acid amplification reactions. In the following description, such substances are referred to as foreign substances not required in analyses of the nucleic acid. Typical examples of the foreign substance are various kinds of protein, sugar and metal ions.

Figure 2B:
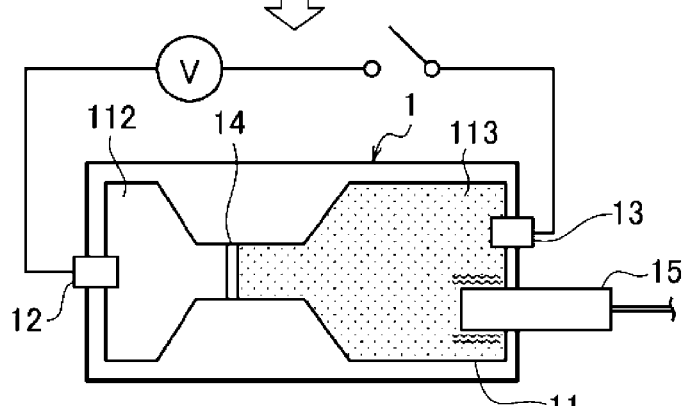

Then, the ultrasonic horn 15 carries out an ultrasonic process on the sample as shown in FIG. 2B. As described above, various kinds of liquid made of a biological material are used as the sample. Thus, by carrying out the ultrasonic process on the sample, it is possible to crush strong membranes in the sample. Typical examples of the strong membranes are a cell membrane, sugar, a lipid membrane and a peptidoglycan layer. The attributes of the ultrasonic process can be properly set in accordance with factors including the type of the sample. The attributes include the frequency and the time duration. In order to crush funguses, viruses and the like with a high degree of precision for example, it is desirable to set the frequency of the ultrasonic process at a value in a range of 10 kHz to 3 MHz and the time duration of the ultrasonic process at a value in a range of five seconds to ten minutes. It is even more desirable to set the frequency of the ultrasonic process at a value of 30 kHz or more.

In addition, in order to promote an operation to crush the membranes described above by carrying out the ultrasonic process, it is desirable to take in bead particles in the negative-electrode side area 113 in advance. The attributes of the bead particle are not prescribed in particular. In this case, the attributes include the size of the bead particle and the type of the particle. That is to say, the attributes of the bead particle can be properly selected in accordance with the sample in use. However, it is possible to make use of an inorganic particle or an organic particle. The inorganic particle can be a zirconia particle, a silica particle, a zeolite particle or the like whereas the organic particle can be an ion exchange resin particle or the like. The use of the zirconia bead having a diameter of about 0.1 mm is desirable in comparison with the other particles. In addition, the bead particles can be put into the negative-electrode side area 113 simultaneously with the introduction of the sample into the channel 11. As an alternative, the bead particles can also be put into the negative-electrode side area 113 in advance prior to the introduction of the sample into the negative-electrode side area 113.

In addition, in order to further promote an operation to crush the membranes described above by carrying out the ultrasonic process, it is desirable to contain a neutral or anionic surface active agent in the sample in advance. The surface active agent can be properly selected in accordance with the type of the sample. Typical examples of the surface active agent are SDS (Sodium Dodecyl Sulfate), Triton-X100, Tween20 and Brij35.

In addition, it is desirable to make use of a buffer solution having a buffering capability in an area having a pH value in a range of 4.0 to 8.0 to serve as the buffer solution for diluting the sample. To put it concretely, it is desirable to make use of a glycine hydrochloric-acid buffer solution, a critic-acid buffer solution, an acetic-acid buffer solution, a critic-acid/phosphoric-acid buffer solution, a phosphoric-acid buffer solution, a tris-hydrochloric-acid buffer solution, MES with a pKa of 6.2, Bis-Tris with a pKa of 6.5, ADA with a pKa of 6.6, PIPES with a pKa of 6.8, ACES with a pKa of 6.9, MOPSO with a pKa of 6.95, BES with a pKa of 7.15 or MOPS with a pKa of 7.2. However, the buffer solution for diluting the sample is not limited to the above.

In addition, the ultrasonic process is carried out in the negative-electrode side area 113. However, the ultrasonic process may also be carried out not necessarily in the negative-electrode side area 113. For example, the ultrasonic process can also be carried out in an area adjacent to the negative-electrode side area 113. In this case, the sample completing the ultrasonic process is injected into the negative-electrode side area 113 through a tube or the like.

Figure 2C:
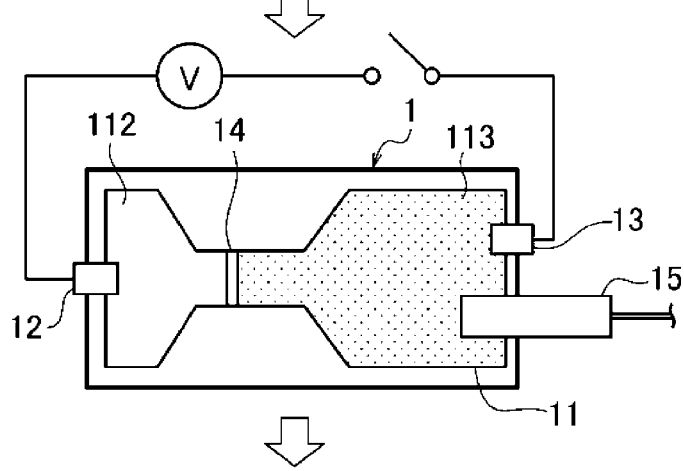

Then, as shown in FIG. 2C, an adsorption carrier adsorbs substances contained in the sample. The substances contained in the sample are mainly foreign substances other than the nucleic acid described above. Thus, the foreign substances are removed from the sample and adsorbed by the adsorption carrier. As a result, the nucleic acid contained in the sample can selectively carry out an electrophoresis movement to be described later with a high degree of precision. In this case, it is desirable to adsorb the foreign substances by adoption of a hydrophobic bonding technique or an electrostatic force technique. For this reason, it is nice to make use of an adsorption carrier particularly having a hydrophobic surface or a negative electric-charge surface. For example, it is desirable to make use of a zeolite, a cation exchange resin or the like. It is more desirable that the zeolite is a high-silica proton-type zeolite whereas the cation exchange resin is a strongly acidic cation exchange resin. In addition, it is even more desirable that the cation exchange resin is a proton-type strongly acidic cation exchange resin. By making use of such an adsorption carrier, it is possible to reduce the pH of the sample and demineralize the sample. It is desirable that the strongly acidic cation exchange resin is a resin having a sulfone-acid radical proton-type ($-SO_3H$) or a sulfone-acid radical natrium-type ($-SO_3Na$) as an exchange group.

The method for adsorbing foreign substances is not prescribed in particular. In accordance with a typical foreign-substance adsorption method, however, the foreign substances are adsorbed by inserting a filter filling up an adsorption carrier into the negative-electrode side area 113 and by passing a sample completing a crushing operation of an ultrasonic process through the filter in a liquid state. In addition, in accordance with an alternative method, prior to the ultrasonic process carried out on the sample as described above, the adsorption carrier is put in the negative-electrode side area 113 in advance and the foreign substances are adsorbed at the same time as the ultrasonic process.

Figure 2D:
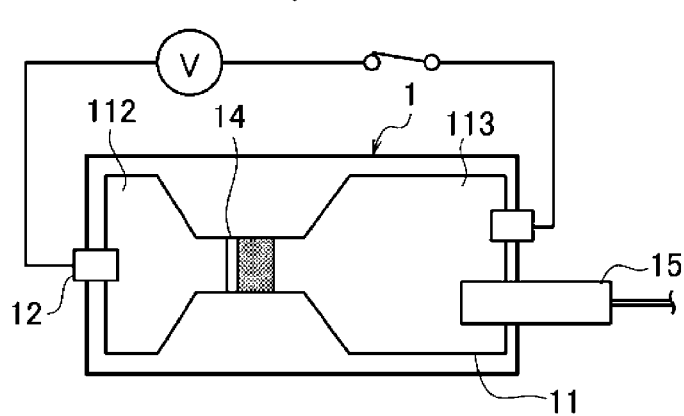

Then, the sample makes an electrophoresis movement as shown in FIG. 2D. The nucleic acid electrically charged with negative electric charge makes an electrophoresis movement through the channel 11 in a direction toward the positive electrode 12. At that time, the dialysis membrane 14 blocks the electrophoresis movement of the nucleic acid and dams the nucleic acid so that the nucleic acid is condensed on the boundary face of the dialysis membrane 14 and in the vicinity of the boundary face. The time duration of the electrophoresis movement is set at a proper value according to the size of the channel 11. For example, it is nice to properly set the time duration of the electrophoresis movement at a typical value in a range of ten seconds to ten minutes. It is to be noted that the boundary face of the dialysis membrane 14 is a surface of contact between the dialysis membrane 14 and the buffer solution filling up the space on the side of the negative-electrode side area 113.

In addition, the buffer solution described above can also be doped with a thickening agent used for increasing the viscosity of the buffer solution. The thickening agent is not prescribed in particular. It is desirable, however, that the buffer solution is one that is capable of controlling the speed of the electrophoresis movement by adjusting the viscosity of the buffer solution. Typical examples of the desirable buffer solution include polyethylene glycol and hydroxy ethyl cellulose. As an alternative, the buffer solution may also be made by blending the typical examples. In addition, by adjusting the viscosity of the buffer solution, it is also possible to reduce redispersion of the nucleic acid. This redispersion of the nucleic acid occurs at the condensation section due to thermal convection which is caused by Joule's heat generated in the course of the electrophoresis movement.

In addition, application of a reversed voltage between the positive electrode 12 and the negative electrode 13 in a short period of time during a process of sucking the buffer solution in the vicinity of the dialysis membrane 14 of the negative-electrode side area 113 is also an effective technique for increasing the quantity of the recovered nucleic acid. By applying a reversed voltage between the positive electrode 12 and the negative electrode 13 in a short period of time during a process of recovering the nucleic acid, the nucleic acid existing on the boundary face of the dialysis membrane 14 can be transferred to the vicinity of the dialysis membrane 14 of the negative-electrode side area 113 so that the nucleic acid can be sucked and recovered by making use of a micropipette. The time duration during which the reversed voltage is applied between the positive electrode 12 and the negative electrode 13 is set at a proper value according to the size of the channel 11. For example, it is nice to properly set the time duration during which the reversed voltage is applied between the positive electrode 12 and the negative electrode 13 at a typical value in a range of one to ten seconds.

Finally, the buffer solution in the vicinity of the dialysis membrane 14 of the negative-electrode side area 113 is sucked by making use of a micropipette in order to recover the condensed nucleic acid.

As described above, in accordance with the nucleic-acid extraction method provided by the present disclosure, after a sample has been introduced into the negative-electrode side area 113, an ultrasonic process is carried out and a process of adsorbing foreign substances from the sample by making use of an adsorption carrier is performed. Then, a nucleic acid is condensed by carrying out an electrophoresis process. In this way, a nucleic-acid amplification reaction can be carried out for the condensed and extracted nucleic acid. It is to be noted that the processes carried out on the sample can be carried out independently of each other or carried out by combining any of the processes which include the ultrasonic process, the adsorption process and the electrophoresis process. For example, after the ultrasonic process and the adsorption process have been carried out at the same time, the electrophoresis process is performed. As an alternative, after the ultrasonic process has been carried out, the adsorption process and the electrophoresis process are performed at the same time. As another alternative, the ultrasonic process, the adsorption process and the electrophoresis process are carried out at the same time.

In addition, as the function of the adsorption carrier used in the nucleic-acid extraction method provided by the present disclosure, it is possible to remove the foreign substances by settling or filtering prior to the execution of the electrophoresis process of the nucleic acid. It is possible to select one of a variety of typical methods as a settling method. The various typical methods include a natural settling method and a settling method making use of a centrifugal force. In addition, as a filtering method, it is possible to adopt a method making use of typically a porous membrane having a shape properly determined in advance in accordance with, among others, the type of the adsorption carrier.

It is desirable that the sample used in the nucleic-acid extraction method provided by the present disclosure is capable of promoting the operation to crush membranes described above in the ultrasonic process and has a pH in a range of 4.0 to 8.0 so that the electrophoresis process can be carried out more smoothly.

In accordance with the nucleic-acid extraction method provided by the present disclosure described above, an ultrasonic process is carried out on a sample, a process of adsorbing foreign substances from the sample by making use of an adsorption carrier is performed and a nucleic acid is condensed by carrying out an electrophoresis process in a series of procedures which can be executed in the same cell. That is to say, the ultrasonic process, the adsorption process and the electrophoresis process can be carried out in the same cell. In other words, it is possible to eliminate the operation to transfer the sample from one cell to another one for every process. Thus, the processing to extract the nucleic acid can be carried out very easily. In addition, the processing to extract the nucleic acid from the sample can be carried out in a short period of time and with a high degree of efficiency.

In addition, in accordance with the nucleic-acid extraction method provided by the present disclosure described above, all the processes are carried out in the same cell and, thus, it is not necessary to transfer the sample from the cell to another apparatus or the like. As a result, when an infectious object of inspection is handled as the sample, it is possible to reduce the risk that the operator is infected by the object of inspection. Also when a blood specimen is used as the sample, the processes ranging from the introduction of the sample into the same area of the nucleic-acid extraction cartridge 1 to the extraction of a nucleic acid can be carried out directly.

In addition, in accordance with the nucleic-acid extraction method provided by the present disclosure described above, by carrying out the ultrasonic process, strong membranes such as a cell membrane, sugar, a lipid membrane and a peptidoglycan layer can be crushed by ultrasonic waves. Thus, the processes according to the nucleic-acid extraction method provided by the present disclosure described above can be carried out without making use of guanidium salts, strong alkali and the like. The guanidium salts are chaotropic ions disturbing nucleic-acid amplification reactions.

In addition, in the nucleic-acid extraction method provided by the present disclosure described above, without making use of strong alkali, enzyme and the like, a cell membrane, an enveloping membrane and a peptidoglycan layer of a gram-positive bacterium can be crushed in an ultrasonic process. Thus, at an inspection time of typically a tuberculosis bacterium in expectorated sputum, it is possible to eliminate, among others, an analyte process based on a reduction agent. As a result, the nucleic acid can be extracted from the sample with ease and with a high degree of precision.

In addition, the ultrasonic process is carried out without performing, among others, a chemical process making use of a special organic solvent. Thus, the membranes described above can be crushed with a high degree of safety and, at the same time, the sample is prevented from deteriorating. On top of that, since the nucleic acid can be extracted without making use of strong alkali, the RNA can be extracted and, at the same time, RNA decomposition caused by the alkali can be avoided.

In addition, in accordance with the nucleic-acid extraction method provided by the present disclosure described above, heating treatments are not required. Thus, the RNA can be extracted and, at the same time, RNA decomposition caused by the heating treatments can be avoided. On top of that, the pH of the buffer solution is set at a value in a range of 4.0 to 8.0 and the ultrasonic process is carried out on the sample under an acidic condition. Thus, the RNase effect can be suppressed.

In addition, in accordance with the nucleic-acid extraction method provided by the present disclosure described above, the foreign substances can be removed by making use of the adsorption carrier. Thus, in the electrophoresis process, only the nucleic acid can be condensed with a high degree of efficiency. As a result, it is possible to precisely detect a target nucleic acid contained in the analyte as an acid having a low concentration.

In addition, in accordance with the nucleic-acid extraction method provided by the present disclosure described above, the nucleic-acid extraction processing can be carried out without performing a process of cleansing the sample. Thus, it is possible to design the nucleic-acid extraction cartridge 1 for carrying out the nucleic-acid extraction method without providing a liquid cutting pump, a centrifuge, a complex solution sending mechanism and the like. As a result, the apparatus configuration of the nucleic-acid extraction cartridge 1 can be simplified and the size of the nucleic-acid extraction cartridge 1 can be reduced as shown in FIG. 1. On top of that, in accordance with the nucleic-acid extraction method provided by the present disclosure as described above, the nucleic-acid extraction processing can be carried out without performing a process of cleansing the sample. Thus, a nucleic acid can be extracted from a sample having a small quantity.

(3) Method for Manufacturing the Nucleic-Acid Extraction Cartridge

The nucleic-acid extraction cartridge 1 according to the first embodiment of the present disclosure is manufactured as follows. The dialysis membrane 14 is inserted into the channel 11 formed inside a base material and the channel 11 is divided into the positive-electrode side area 112 and the negative-electrode side area 113 by the dialysis membrane 14. The adsorption carrier is accommodated in the negative-electrode side area 113 and the ultrasonic horn 15 is provided in the negative-electrode side area 113.

The channel 11 is formed inside the base material, which is a glass base material, typically by carrying out a wet etching process or a dry etching process on the base material. As an alternative, the channel 11 can also be formed inside the base material by carrying out a cutting process or the like on the plastic base material. It is to be noted that one, two or more channels can be formed in the nucleic-acid extraction cartridge 1.

It is desirable to make each of the positive electrode 12 and the negative electrode 13 of gold (Au) or platinum (Pt) by carrying out a sputtering process or an evaporation process. In this respect, inside a nucleic-acid extraction cartridge according to a related technology, a platinum wire is used for the electrodes in some configurations. In this case, every time an experiment is carried out, it is necessary to put the platinum wires in the nucleic-acid extraction cartridge. In addition, the price of the platinum wires is high. Taking these factors into consideration, the nucleic-acid extraction cartridge cannot be made disposable. As described above, on the other hand, in the case of the nucleic-acid extraction cartridge 1 according to this embodiment, each of the positive electrode 12 and the negative electrode 13 is made of gold (Au) by carrying out a sputtering process or an evaporation process in order to form the positive electrode 12 and the negative electrode 13 in the nucleic-acid extraction cartridge 1 in advance. Thus, the nucleic-acid extraction cartridge 1 according to this embodiment can be handled with ease. In addition, in comparison with the nucleic-acid extraction cartridge according to the related technology, the nucleic-acid extraction cartridge 1 according to this embodiment can also be made disposable. Thus, in the case of the nucleic-acid extraction cartridge 1 according to this embodiment, the sample can be prevented from being contaminated.

The ultrasonic horn 15 can be designed properly into any configuration as long as the configuration allows the ultrasonic process to be carried out on the sample. For example, the ultrasonic horn 15 can be embedded in the base material.

Figure 3:
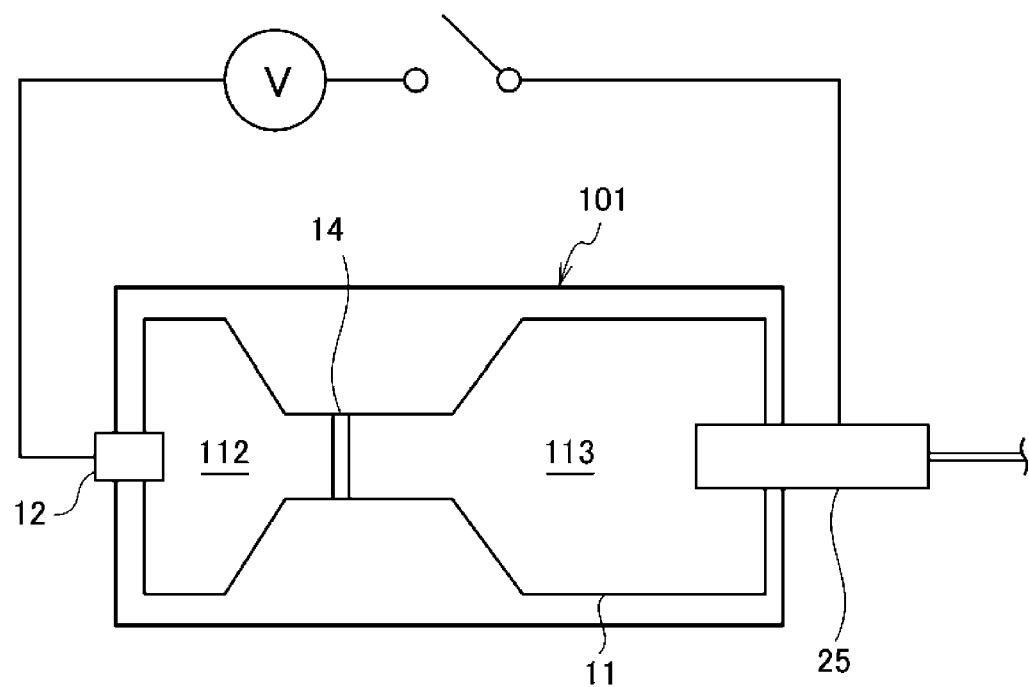
FIG. 3 is an explanatory model diagram showing the configuration of a nucleic-acid extraction cartridge according to a modified version of the first embodiment of the present disclosure.

2. A Nucleic-Acid Extraction Cartridge According to a Modified Version of the First Embodiment of the Present Disclosure, a Nucleic-Acid Extraction Method for the Cartridge and a Method for Manufacturing the Nucleic-Acid Extraction Cartridge Next, by referring to FIG. 3, the following description explains a nucleic-acid extraction cartridge 101 according to a modified version of the first embodiment of the present disclosure. FIG. 3 is an explanatory model diagram showing the configuration of the nucleic-acid extraction cartridge 101 according to the modified version of the first embodiment of the present disclosure. It is to be noted that, in this modified version of the embodiment, each element having a functional configuration substantially identical with its counterpart employed in the embodiment is denoted by the same reference numeral as the counterpart and the explanation of such an identical element is omitted in order to avoid duplications of descriptions.

The channel 11, the positive electrode 12, the negative electrode 13 and the dialysis membrane 14 which are employed in the nucleic-acid extraction cartridge 101 according to the modified version of the embodiment have functional configurations identical with respectively those of the channel 11, the positive electrode 12, the negative electrode 13 and the dialysis membrane 14 which are employed in the nucleic-acid extraction cartridge 1 according to the embodiment. Except that the negative electrode 13 and the ultrasonic horn 15 are implemented by the same member which is an electrode/ultrasonic horn 25 in the nucleic-acid extraction cartridge 101 according to the modified version of the embodiment, the nucleic-acid extraction cartridge 101 is substantially identical with the nucleic-acid extraction cartridge 1 according to the embodiment. For this reason, the following description explains only the same member which is the electrode/ultrasonic horn 25 implementing the negative electrode 13 and the ultrasonic horn 15.

The nucleic-acid extraction method provided by the modified version of the embodiment and the method for manufacturing the nucleic-acid extraction cartridge 101 according to the modified version are identical with respectively the nucleic-acid extraction method provided by the embodiment and the method for manufacturing the nucleic-acid extraction cartridge 1 according to the embodiment except that, in the nucleic-acid extraction cartridge 101 according to the modified version, the negative electrode 13 and the ultrasonic horn 15 are implemented by the same member which is the electrode/ultrasonic horn 25. For this reason, the explanation of these methods are omitted in order to avoid duplications of descriptions.

Since the electrode/ultrasonic horn 25 has a functional configuration identical with that of the negative electrode 13 explained earlier, the electrode/ultrasonic horn 25 can be properly made of gold (Au) or platinum (Pt) by carrying out a sputtering process or an evaporation process. In addition, since the electrode/ultrasonic horn 25 has a functional configuration identical with that of the ultrasonic horn 15 described before, the attributes of the electrode/ultrasonic horn 25 are not prescribed in particular. In this case, the attributes include the shape of the electrode/ultrasonic horn 25. That is to say, the electrode/ultrasonic horn 25 can be any member as long as this member is capable of carrying out the ultrasonic process on the sample in accordance with the nucleic-acid extraction method. It is even possible to make use of typically an ultrasonic probe in place of the ultrasonic horn 15.

It is to be noted that the present disclosure can be realized as the following implementations:

(1) A nucleic-acid extraction method for carrying out the following procedures in the same cell, the procedures including:
performing an ultrasonic process on a sample containing a nucleic acid;
adsorbing substances contained in the sample by making use of an adsorption carrier; and
condensing the nucleic acid by damming the nucleic acid moving in an electrophoresis phenomenon.

(2) The nucleic-acid extraction method according to implementation (1), wherein a cation exchange resin or a zeolite is used as the adsorption carrier.

(3) The nucleic-acid extraction method according to implementation (2), wherein a strongly acidic cation exchange resin is used as the cation exchange resin.

(4) The nucleic-acid extraction method according to any one of implementations (1) to (3), wherein the ultrasonic process is carried out after blending bead particles in the sample.

(5) The nucleic-acid extraction method according to any one of implementations (1) to (4), wherein the substances are each a foreign substance other than the nucleic acid.

(6) The nucleic-acid extraction method according to any one of implementations (1) to (5),
wherein the procedure of performing the ultrasonic process on the sample is a procedure of performing the ultrasonic process on the sample by diluting the sample by making use of a buffer solution, and
the pH of the buffer solution has a value in a range of 4.0 to 8.0.

(7) The nucleic-acid extraction method according to any one of implementations (1) to (6), wherein the buffer solution contains a thickening agent.

(8) The nucleic-acid extraction method according to any one of implementations (1) to (7), wherein the thickening agent contains polyethylene glycol and/or hydroxy ethyl cellulose.

(9) A nucleic-acid extraction cartridge including:
a channel allowing a sample containing a nucleic acid to be introduced into the channel;
electrodes each provided on one of the ends of the channel;
a damming section configured to divide the channel into a negative-electrode side area and a positive-electrode side area and dam the nucleic acid;
an adsorption carrier provided in the negative-electrode side area to adsorb substances contained in the sample; and
an ultrasonic-wave generation section configured to carry out an ultrasonic process on the sample.

(10) The nucleic-acid extraction cartridge according to implementation (9), wherein the ultrasonic-wave generation section is implemented as the same member as one of the electrodes.

(11) The nucleic-acid extraction cartridge according to implementation (9) or (10), wherein the damming section is a dialysis membrane or a polymer gel.

(12) The nucleic-acid extraction cartridge according to any one of implementations (9) to (11), wherein the ultrasonic-wave generation section is an ultrasonic probe or an ultrasonic horn.

EXAMPLES

1. Verification of the Adsorption Quantity for the Adsorption Carrier of the Sample (1-1. Nucleic-Acid Refining Capacity by Zeolite)

Proton-type zeolite having a quantity of 100 mg was put in a spin filter column (Ultrafree-M, 0.45 μm). Then, a 50 mM MES buffer containing 0.5% SDS and having a pH of 5 was adjusted and BSA was added thereto so as to attain 0.5%. In addition, Cy3-modified 20 mer oligo DNA was added thereto so as to attain 5 μM. After blended liquid obtained as a result of blending this protein with a nucleic acid had been agitated adequately at normal temperature, the liquid having an amount of 200 ul was dropped to a zeolite encapsulating spin column and well agitated. Then, a centrifugation processing was carried out for two minutes at 12,000 G in order to spin down the blended liquid. Subsequently, the spun-down liquid was subjected to an absorbed-light measurement carried out at a nanodrop level. From a difference between the degree of light absorption before the zeolite processing and the degree of light absorption after the zeolite processing, the nucleic-acid refining capacity was evaluated. The BSA light absorption degree was evaluated in a protein A280 mode whereas the light absorption degree of the nucleic acid was evaluated as a Cy3 light absorption degree in a microarray mode. Results of the evaluation are shown in FIG. 4.

Figure 4:
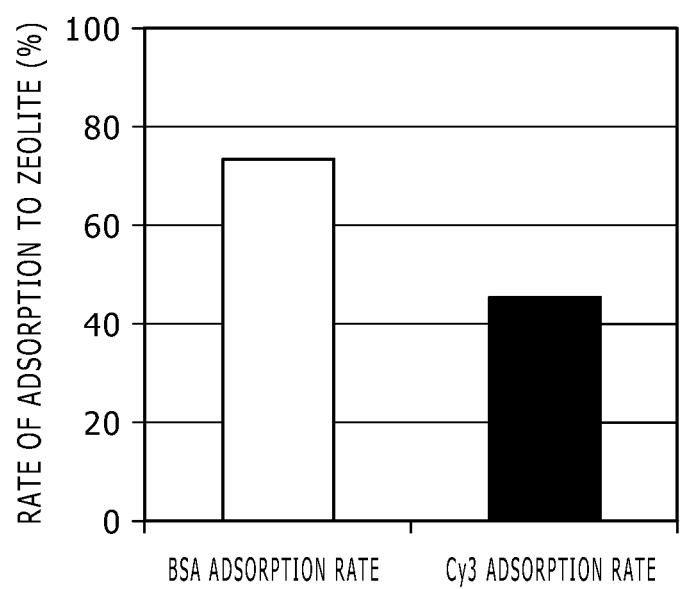
FIG. 4 shows graphs each representing the adsorption rate for a zeolite for a sample.

As shown in FIG. 4, from a reduction in BSA concentration from the degree of light absorption before the zeolite processing to the degree of light absorption after the zeolite processing, the quantity of adsorption to the zeolite was found to be about 70%. On the other hand, the non-peculiar adsorption quantity of the nucleic acid was found to be about 45%. From these facts, it has been possible to verify that, by carrying out the zeolite processing, the DNA existence ratio can be raised even in a blended system obtained as a result of blending protein with a nucleic acid (refer to FIG. 4).

(1-2. Nucleic-Acid Refining Capacity by Strongly Acidic Cation Exchange Resin)

Strongly acidic cation exchange resin (Nuvia S made by Bio Rad Company) having a quantity of 100 mg was put in a spin filter column (Ultrafree-M, 0.45 µm). Then, a 50 mM MES buffer having a pH of 5 was adjusted and BSA was added thereto so as to attain 0.5%. In addition, Cy3-modified 20 mer oligo DNA was added thereto so as to attain 5 µM. After blended liquid obtained as a result of blending this protein with a nucleic acid had been agitated adequately at normal temperature, the liquid having an amount of 200 ul was dropped to a spin column encapsulating the strongly acidic cation exchange resin and well agitated. Then, a centrifugation processing was carried out for two minutes at 12,000 G in order to spin down the blended liquid. Subsequently, the spun-down liquid was subjected to an absorbed-light measurement carried out at a nanodrop level. From a difference between the degree of light absorption before the processing of the strongly acidic cation exchange resin and the degree of light absorption after the processing of the strongly acidic cation exchange resin, the nucleic-acid refining capacity was evaluated. The BSA light absorption degree was evaluated in a protein A280 mode whereas the light absorption degree of the nucleic acid was evaluated as a Cy3 light absorption degree in a microarray mode. Results of the evaluation are shown in FIG. 5.

Figure 5:
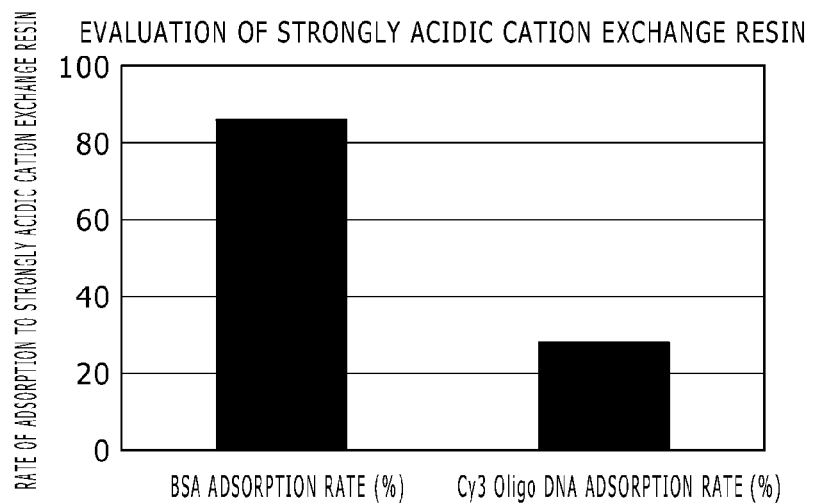
FIG. 5 shows graphs each representing the adsorption rate for a strongly acidic cation exchange resin of a sample.

As shown in FIG. 5, from a reduction in BSA concentration from the degree of light absorption before the processing of the strongly acidic cation exchange resin to the degree of light absorption after the processing of the strongly acidic cation exchange resin, the quantity of adsorption to the strongly acidic cation exchange resin was found to be about 85%. On the other hand, the non-peculiar adsorption quantity of the nucleic acid was found to be about 28%. From these facts, it has been possible to verify that, by carrying out the processing of the strongly acidic cation exchange resin, the DNA existence ratio can be raised even in a blended system obtained as a result of blending protein with a nucleic acid (refer to FIG. 5).

2. LAMP Reactions and RT-LAMP Reactions

First Example

<Ultrasonic Process>

Bifidobacteria were added to EDTA blood-drawing bovine whole blood so as to attain a concentration of 1,000 bacteria/uL. Then, the bifidobacteria and the blood which together had a quantity of 1 mL were injected into a polypropylene tube having a capacity of 2 mL. Subsequently, the ultrasonic horn was immersed and a crushing process was carried out for two minutes at a vibration frequency of 40 kHz.

<Adsorption Process>

Then, proton-type zeolite having a quantity of 100 mg was put in a spin filter column (Ultrafree-M, 0.45 µm). Subsequently, after blended liquid obtained as a result of blending the protein with a nucleic acid had been agitated adequately at normal temperature, the liquid having an amount of 200 ul was dropped to a zeolite encapsulating spin column and well agitated.

<Electrophoresis>

Then, a DC voltage of 100V was applied between the electrodes 12 and 13 of the nucleic-acid extraction cartridge 1 for a period of 20 minutes in order to carry out an electrophoresis process on the sample.

<LAMP Reactions>

Subsequently, the sample, the enzyme, the fluorescent isothiocyanate, the nucleic-acid monomer, the buffer, the primer set for the target nucleic-acid chain amplification and the probe for real-time measurements were combined with each other in order to prepare LAMP-reaction liquid. The LAMP reaction was measured by making use of a thermal cycler Chromo4 made by Bio Rad, a US company, to serve as a cycler capable of carrying out real-time measurements. The used probe was a QP probe which was a quenching probe so that the amplification of the nucleic acid and the decrease of the fluorescence intensity can be observed. For more information on the QP probe which is J-bio21, refer to a Japanese website http://www.j-bio21.co.jp/tech/qp-method.htm dated Jul. 19, 2011 with a title of "QP Method."

(Results)

Figure 6:
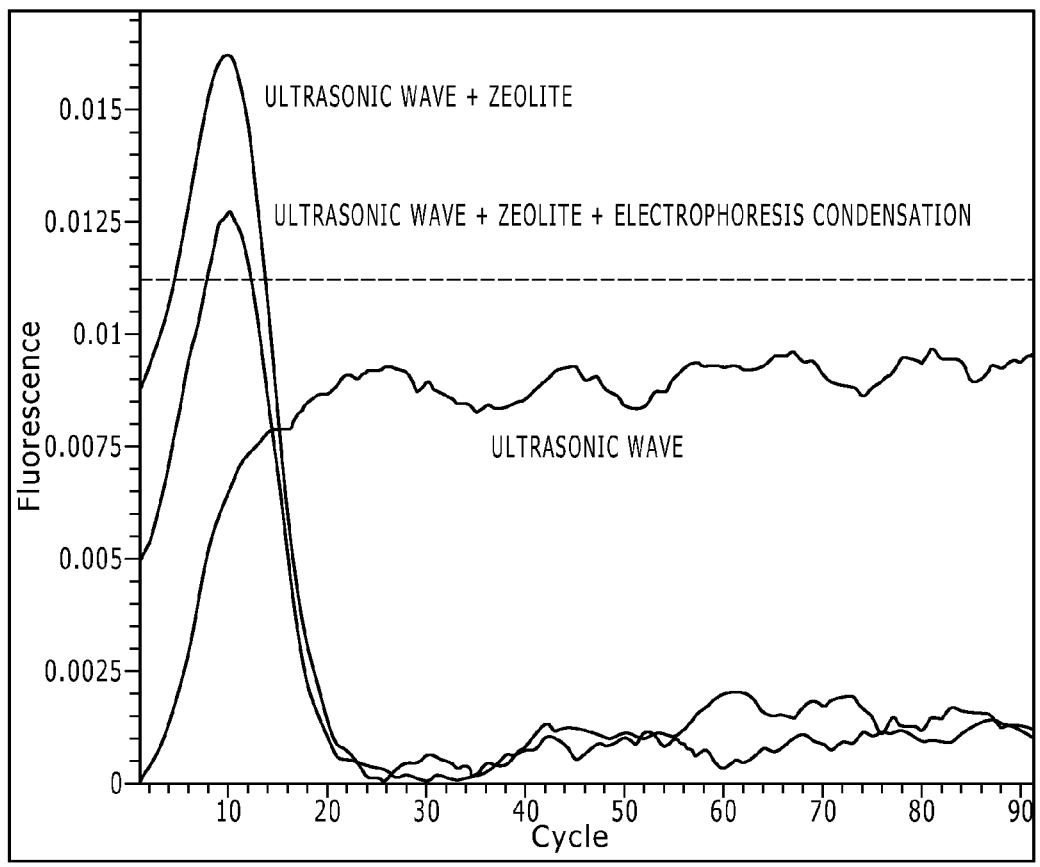
FIG. 6 shows graphs representing results of LAMP reactions of a sample.

FIG. 6 is a diagram showing results extracted from processes of preprocessing to serve as results of evaluations of LAMP reactions. A result marked with "ultrasonic wave" in the figure is a result of a real-time measurement of target nucleic-acid chain amplification quantities for a case in which a sample completing only an ultrasonic crushing process is used. In addition, a result marked with "ultrasonic wave+zeolite" in the figure is a result of a real-time measurement of target nucleic-acid chain amplification quantities for a case in which a sample completing an ultrasonic crushing process and an adsorption process is used. On top of that, a result marked with "ultrasonic wave+zeolite+electrophoresis condensation" in the figure is a result of a real-time measurement of target nucleic-acid chain amplification quantities for a case in which a sample completing an ultrasonic crushing process, an adsorption process and an electrophoresis condensation process is used.

As shown in FIG. 6, the amplification reaction of the nucleic acid for a sample completing only an ultrasonic crushing process was not detected. In the case of a sample completing a zeolite process, on the other hand, the fluorescence quenching could be verified. In addition, in the case of a sample completing an ultrasonic crushing process, a zeolite process and an electrophoresis condensation process, it was possible to verify the fact that the start timing of the quenching was expedited. That is to say, it is obvious that the zeolite process eliminates reaction disturbing substances as well as foreign substances and the electrophoresis process allows condensation of the target nucleic acid.

The nucleic-acid extraction method provided by the present disclosure allows operations to be carried out with ease and is capable of extracting a nucleic acid from a sample in a short period of time with a high degree of efficiency. Thus, the nucleic-acid extraction method can be applied to nucleic-acid extraction processing for nucleic-acid amplification reactions according to, among other methods, the PCR (Polymerase Chain Reaction) method or the LAMP (Loop-Mediated Isothermal Amplification) method. In addition, the nucleic-acid extraction method can also be adopted for detecting a nucleic acid from a sample which contains the nucleic acid having only a small quantity or has an extremely low concentration.

The present disclosure contains subject matter related to that disclosed in Japanese Priority Patent Application JP 2011-158991 filed in the Japan Patent Office on Jul. 20, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A nucleic-acid extraction method, the method comprising:
    inserting a sample containing a nucleic-acid into a negative-electrode side area between a dialysis membrane and a negative electrode;
    performing an ultrasonic process on the sample containing a nucleic-acid and adjusting the time and frequency of the ultrasonic process based on the type of the sample;
    adsorbing foreign substances contained in the sample using an adsorption carrier after performing the ultrasonic process; and
    blocking an electrophoresis movement of the nucleic acid to condense the nucleic-acid on a boundary face of the dialysis membrane after adsorbing the foreign substances, wherein
    bead particles are inserted into the negative-electrode side area before the sample containing the nucleic-acid is inserted into the negative-electrode side area.

2. The nucleic-acid extraction method according to claim 1, wherein a cation exchange resin or a zeolite is used as the adsorption carrier.

3. The nucleic-acid extraction method according to claim 2, wherein a strongly acidic cation exchange resin is used as the cation exchange resin.

4. The nucleic-acid extraction method according to claim 1, further comprising blending the bead particles in the sample, and wherein the ultrasonic process is performed after blending the bead particles in the sample.

5. The nucleic-acid extraction method according to claim 1, wherein the foreign substances are each a substance other than the nucleic acid.

6. The nucleic-acid extraction method according to claim 1, further comprising diluting the sample with a buffer solution, wherein the ultrasonic process is performed on the sample after diluting the sample with the buffer solution, and wherein the pH of the buffer solution is between 4.0 and 8.0.

7. The nucleic-acid extraction method according to claim 6, wherein the buffer solution contains a thickening agent.

8. The nucleic-acid extraction method according to claim 7, wherein the thickening agent contains at least one of polyethylene glycol or hydroxy ethyl cellulose.

* * * * *